(12) United States Patent
Wu

(10) Patent No.: US 6,696,094 B2
(45) Date of Patent: *Feb. 24, 2004

(54) HERBAL PHARMACEUTICAL COMPOSITION FOR TREATMENT OF HIV/AIDS PATIENTS

(76) Inventor: Tzu-Sheng Wu, 19F, No. 171, Cheng-Kung Road, Sanchung, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 10/208,050

(22) Filed: Jul. 31, 2002

(65) Prior Publication Data

US 2003/0091658 A1 May 15, 2003

Related U.S. Application Data

(63) Continuation-in-part of application No. 09/906,791, filed on Jul. 18, 2001, now Pat. No. 6,455,078.
(60) Provisional application No. 60/240,963, filed on Oct. 18, 2000.

(51) Int. Cl.[7] ............... A61K 35/78; A61K 35/37; A61K 35/407
(52) U.S. Cl. ............... 424/725; 424/728; 424/773; 424/777; 424/551; 424/553
(58) Field of Search ................. 424/725, 728, 424/773, 777, 551, 553

(56) References Cited

U.S. PATENT DOCUMENTS

| 5,178,865 A |   | 1/1993  | Ho et al.   |
|-------------|---|---------|-------------|
| 5,837,257 A | * | 11/1998 | Tsai et al. |
| 5,989,556 A |   | 11/1999 | Tsai et al. |

FOREIGN PATENT DOCUMENTS

| CN | 8800048   | * | 10/1988 |
|----|-----------|---|---------|
| CN | 1151312 A |   | 7/1996  |
| CN | 1148983   | * | 5/1997  |
| CN | 1151312   | * | 6/1997  |

* cited by examiner

Primary Examiner—Christopher R. Tate
(74) Attorney, Agent, or Firm—Fei-Fei Chao; Venable LLP (57) ABSTRACT

The present invention provides a pharmaceutical composition for treating patients with HIV infection. The pharmaceutical composition is in the form of an intravenous injection solution and optionally capsules. The pharmaceutical composition contains fourteen (14) ingredients, i.e., diffuse hedyotis, bistort rhizome, giant knotweed rhizome, Asiatic moonseed rhizome, baical skullcap root, bovine biliary powder, milkvetch root, barbary wolfberry fruit, sanqi, figwort root, Chinese magnoliavine fruit, turmeric root-tuber, hawthorn fruit, and Chinese angelica.

18 Claims, 1 Drawing Sheet

FIG. 1

HERBAL PHARMACEUTICAL COMPOSITION FOR TREATMENT OF HIV/AIDS PATIENTS

CROSS-REFERNCE TO RELATED APPLICATION

The present application is a continuation-in-part (CIP) of U.S. patent application Ser. No. 09/906,791 filed on Jul. 18, 2001, now U.S. Pat. No. 6,455,078 which in turn claims the priority of U.S. Provisional Application No. 60/240,963 filed on Oct. 18, 2000. Both U.S. priority applications are herein incorporated by reference.

FIELD OF THE INVENTION

The present invention relates to a novel herbal pharmaceutical composition and its use for treating patients with human immunodeficiency virus (HIV) infection. The pharmaceutical composition is in the form of an intravenous injection solution or capsules and contains aqueous extracts of fourteen (14) herbal ingredients, including diffuse hedyotis, bistort rhizome, giant knotweed rhizome, Chinese magnoliavine fruit, Asiatic moonseed rhizome, baical skullcap root, bovine biliary powder, tumeric root-tuber, hawthorn fruit, sanqi, barbary wolfberry fruit, figwort root, Chinese angelica, and milkvetch root. The intravenous injection solution can be administered alone or co-administered with the capsules. The present invention also includes the methods for making the pharmaceutical composition and for treating the patients with HIV infection.

DESCRIPTION OF THE RELATED ART

The present invention is a continuation-in-part (CIP) of the parent patent application, U.S. patent application Ser. No. 09/906,791, now U.S. Pat. No. 6,455,078, which is herein incorporated by reference. In the parent application, novel pharmaceutical compositions, which are particularly effective in treating patients with human immunodeficeincy virus (HIV), were described.

HIV infection causes acquired immunodeficiency syndromes (AIDS) in humans which presents special problems to the medical community. AIDS is a pandemic immunosuppressive disease which results in life-threatening opportunistic infections and malignancies. The retrovirus, HIV, has been isolated and identified as the etiologic agent of this disease. HIV has been detected in whole blood, plasma, lymphatic fluid, serum, semen, vagina fluid, breast milk, tears, saliva, and central nervous system tissue of infected patients. HIV can be transmitted through sexual contact with an infected person, by sharing needles or syringes (primarily for drug injection) with an infected person, or, less commonly, through transfusions of infected blood or blood clotting factors. Babies born to HIV-infected women may become infected before or during birth or through breast-feeding after birth. As of this time, complete cure for HIV infection/AIDS has been diligently pursued by scientists around the world, yet there has been no report of absolute success.

Pharmaceutical compositions made from natural herbs have been known and used for thousands of years to cure or ameliorate various diseases and injuries. Some of these herbal compositions have been disclosed for having medicinal properties for curing or ameliorating symptoms associated with HIV infection. For example, U.S. Pat. No. 5,178,865 discloses screening of fifty-six (56) individual herbs and have found that ten (10) out of 56 herbs exhibits anti-HIV activity in ex vivo experiments. The ten (10) individual herbs include *Coptis chineusis, Ligusticum wallichii, Illicium lanceolatum, Isatis tinctoria, Salvia miltiorrhiza, Erycibe obtusifolia, Acanthopanax graciliatylus, Bostaurus domesticus, Inula helenium*, and *Lonicera japonica*. Both *Bostaurus domesticus* and *Lonicera japonica* are further described to be able to combine with *Scutellaria baicaleusis* to exhibit anti-HIV activity.

U.S. Pat. No. 5,837,257 discloses Chinese herbal medicines that exhibit in vitro antiviral activities against murine leukemia virus and HIV and for treatment of animals and humans infected with HIV. In one of the preferred embodiments, the Chinese herbal medicines contain hedyotis, scutellariae barbatae herba, lonicerae flos, prunellae spica, and solani herba.

U.S. Pat. No. 5,989,556 discloses various herbal compositions for treating viral infection. One of the herbal compositions contains Aeginetiae Herba, Blechni Rhizoma, Lespedezae Herba, Polygoni Cuspidati Rhizoma, Forsythiae Fructus, and Ligustri Fructus. Another herbal composition contains Cirsii Rhizoma et Radix, Breeae Radix, Baphicacanthis Rhizoma et Radix, Phellodendri Cortex, and Bletillae Tuber. A third herbal composition disclosed in the patent has Aeginetiae Herba, Lonicerae Flos, Prunellae Spica, and Lespedezae Herba.

The present invention provides a novel pharmaceutical composition for treatment of HIV, both in vitro and in vivo, including treatment of AIDS patients, which are distinctively different from prior art disclosures. This novel pharmaceutical composition differs from the pharmaceutical compositions described in the parent application for not containing red ginseng (Radix *ginseng rubra*). The pharmaceutical composition of the present invention is a natural Chinese medicine with little or no side effects and has no toxicity.

SUMMARY OF THE INVENTION

The present invention provides a pharmaceutical composition which is particularly effective in treating HIV-positive or AIDS patients. The pharmaceutical composition (in the name of "HIVCIDE") is in the form of an injection solution (for intravenous injection) or capsules. It contains aqueous extract of the following herbal ingredients: (1) an entire plant of Herba *Hedyotidis diffusae* (diffuse hedyotis); (2) a rhizome of Rhizoma Bistortae (bistort rhizome); (3) a rhizome of Rhizoma *Polygoni Cuspidati* (giant knotweed rhizome); (4) a ripe fruit of Fructus Schisandrae (Chinese magnoliavine fruit); (5) a rhizome of Rhizoma Menispermi (Asiatic moonseed rhizome); (6) a root of Radix Scutellariae (baical skullcap root); (7) bovine biliary powder; (8) a root tuber of Radix Curcumae (tumeric root-tuber); (9) a ripe fruit of Fructus Crataegi (hawthorn fruit); (10) a root of Radix Notoginseng (sanqi); (11) a ripe fruit of Fructus Lycii (barbary wolfberry fruit); (12) a root of Radix Scrophulariae (figwort root); (13) a root of Radix *Angelicae sinensis* (Chinese angelica); and (14) a root of Radix Astragali (milkvetch root). Examples of the aqueous solution for extracting the pharmaceutical ingredients from the herbs include, but are not limited to, water, ethanol, or a mixture thereof. The preferred aqueous solution is water.

The herbal ingredients of HIVCIDE differ from that in the parent application by not containing the root of Radix *ginseng rubra* (red ginseng). Also, the weight ratio of the pharmaceutical composition of the present invention is different from that of the pharmaceutical composition of the parent application by containing more quantity of diffuse hedyotis. The weight ratio of the 14 ingredients listed above is about 4:3:1:2:1:1:0.1:1:2:1:3:2:1:2.

The aqueous extract of the herbal ingredients is further filtered and condensed. The condensed aqueous extract is called "herbal condensate" or "HIVCIDE condensate." The volume of the herbal filtrate is about 1.4 fold of the herbal condensate.

The gram weight of the HIVCIDE for the purpose of determining the dosage amounts for patient treatment as described hereinafter is based on the weight of the "HIVCIDE condensate," not the weight of the original herbal ingredients.

The present invention also includes a method for preparing HIVCIDE which includes the steps of: (1) grinding and mixing diffuse hedyotis, bistort rhizome, giant knotweed rhizome, Chinese magnoliavine fruit, Asiatic moonseed rhizome, baical skullcap root, bovine biliary powder, tumeric root-tuber, hawthorn fruit, sanqi, barbary wolfberry fruit, figwort root, Chinese angelica, and milkvetch root to form a herbal mixture; (2) boiling the herbal mixture in water to form a water extract; (3) filtering the water extract to collect an herbal filtrate; and (4) concentrating the herbal filtrate to form an herbal condensate (also known as "HIVCIDE condensate"). The HIVCIDE condensate is then either dissolved in a suitable solution to form the intravenous injection solution or sprayed dried to form herbal powders. The herbal powders are further mixed with a binder, such as starch, and encapsulated.

The HIVCIDE injection solution contains about 0.1–1 g of the HIVCIDE condensate per ml of the injection solution. When administering to patients, the HIVCIDE is perferably diluted to about 1:5 to 1:10 by volume of 5% glucose solution.

The present invention further contains a method for treating patients with HIV infection which includes intravenous administration of an effective amount of HIVCIDE to patients with HIV infection. The preferred dosage is about 1 to 10 g of HIVCIDE condensate, most preferably, about 2–6 g of HIVCIDE condensate, per day.

Additionally, the present invention provides a method for treating patients with HIV infection which comprises: intravenous administering the HIVCIDE injection solution and orally administering the HIVCIDE capsules to patients. The preferred dosage of the HIVCIDE injection solution is about 1 to 10 g, most favorably, 2–6 g, of the HIVCIDE condensate per day, preferrably in one injection.

The preferred dosage for HIVCIDE capsules is about 0.1 to 2 g of HIVCIDE condensate per serving and for about 2–4 times a day.

BRIEF DESCRIPTION OF THE DRAWING

FIG. 1 shows the HIV numbers in the five HIV positive patients as described in EXAMPLE 5, infra. These five HIV-positive patients were treated with daily intravenous injection of HIVCIDE injection solution (Example 1, infra) for 3 months. Patient #1 (→, solid line with solid arrow) had received AZT and DDI treatment for 3 months. Ten (10) days after the discontinuance of the AZT and DDI treatment, patient #1 started the HIVCIDE daily injection. Patient #5 (→, solid line with open arrow) received the HIVCIDE treatment concurrently with α-interferon. Results for Patents #2, #3 and #4 are indicated as → (dash line with solid arrow), -● (solid line with solid circle) and ••• ● (dash line with solid circle), respectively.

DETAILED DESCRIPTION OF THE INVENTION

Traditional Chinese medicine has been in existence for more than two thousand years. It has a proven record of success for curing many kinds of diseases. Traditional Chinese medicine utilizes a variety of herbs and natural substances. Each herb/natural substance has its unique characteristics. By combining and balancing the unique characteristics of herbs, a doctor can prescribe a formulation with enhanced medicinal activities and with less or no toxicity by synergizing the medicinal effects among various herbs, while in the meantime, cancelling out or neutralizing the toxic effects of the herbs. This, in Chinese herbal medicine, is regarded as to regulate between negative/hypoactive characteristics ("yin") and positive/hyperactive characteristics ("yang"), Under the definitions set forth in the traditional Chinese medicine, "yin" is defined as drugs which cure cold syndrome (which itself has hot or warm property), and "yang" is defined as drugs which cure heat syndrome (which itself has cold or cool property).

The pharmaceutical combination of the present invention comprises fourteen (14) ingredients, which are particularly effective in treating patients with HIV. Out of the 14 ingredients, four (4) ingredients are the core ingredients which contribute to the primary efficacy and healing effect of the composition. They are: (1) diffuse hedyotis/spreading hedyotis (Pharmaceutical name: Herba *Hedyotidis diffusae*; Botanical name: *Hedyotis diffusa* Willd.); (2) bistort rhizome (Pharmaceutical name: Rhizoma Bistortae; Botanical name: *Polygonum bistorta* L.); (3) giant knotweed rhizome (Pharmaceutical name: Rhizoma *Polygoni Cuspidati*; Botanical name: *Polygonum cuspidatum* Sieb. et Zucc.), and (4) Chinese magnoliavine fruit (Pharmaceutical name: Fructus Schisandrae Chinensis; Botanical name: *Schisandra chinensis* (Turcz.) Baill., S. sphenanthera Rehd. et Wils.). The core ingredients are functioned in clearing heat and toxic substances while improving immune system and circulation, curing symptoms of jaundice, and having beneficial effect on internal organs.

There are six (6) additional ingredients that are used to improve and balance the pharmaceutical effects activities produced by the above named core ingredients. These six ingredients also have toning effect and can improve blood circulation in the liver. These six ingredients are: (1) Asiatic moonseed rhizome (Pharmaceutical name: Rhizoma Menispermi; Botanical name: *Menisermum dauricum* DC); (2) baical skullcap root (Pharmaceutical name: Radix Scutellariae; Botanical name: *Scutellaria baicalensis* Georgi); (3) bovine biliary powder (Zoological name: *Vesica Fellea Bovus*); (4) tumeric root-tuber (Pharmaceutical name: Radix Curcumae; Botanical name: Curcuma wenyujin Y. H. Lee et Cl Ling); (5) Hawthorn Fruit (Pharmaceutical name: Fructus Crataegi; Botanical name: *Crataegus pinnatifida* Bge.); and (6) sanqui (Pharmaceutical name: Radix Notoginseng; Botanical name: *Panax notoginseng* (Burk.)).

Finally, there are additional five (4) ingredients which are used to primarily provide nutrients and energy sources for patients so as to expedite the recovery process. These ingredients include: (1) barbary wolfberry fruit (Pharmaceutical name: Fructus Lycii; Botanical name: *Lycium barbarum* L.); (2) figwort root (Pharmaceutical name: Radix Scrophulariae; Botanical name: *Scrophularia ningpoensis*); (3) Chinese angelica (Pharmaceutical name: Radix *Angelicae sinensis*; Botanical name: *Angelica sinensis* (Oliv.) Diels); and (4) milkvetch root (Pharmaceutical name: Radix Astragali; Botanical name: *Astragalus membranaceus* (Fisch.) Bge.). Among these ingredients, milkvetch root (Radix Astragali) also has the capacity of improving immunological functions of the body to fense off diseases.

The pharmaceutical composition of the present invention differs from the composition described in the parent application by not containing red ginseng (Radix *Ginseng Rubra*). It was found that the presence of red ginseng appeared to cause relapse of the disease after termination of the use of the pharmaceutical composition. Also, the pharmaceutical composition of the present invention is particularly suitable for intravenous injection and less effective for oral administration, which is also slightly different from the pharmaceutical composition of the parent application, where both capsules (in the form of HIVCIDE powder) and intravenous injection are effective.

The pharmaceutical names, botanical or zoological names, family names, common descriptions, and major ingredients of the herbs used in the present invention are shown in Table 1.

TABLE 1

Herbs of the Present Pharmaceutical Composition

| Pharmaceutical Name | Botanical/ Zoological Name | Family | Common Description | Major Ingredients |
|---|---|---|---|---|
| Herba Hedyotidis Difffusae | *Heydyotis diffusa* (Willd.) Roxb., also known as *Oldenlandia diffusa* | Rubiaceae | heydyotis, oldenlandia | hentriacontane, stigmastatrienol, ursolic acid, oleanolic acid, β-sitosterol, ρ-coumaric, β-sitosterol-D-glucoside |
| Radix et Rhizoma Polygoni Cuspidati | *Polygonum cuspidatum* Sieb. et Zucc. | Polygonaceae | Giant Knotweed root and Rhizome | emodin, chryso-phanol, rheic acid, emodin monomethyl ether, polygonim, and physcion-8-β-D-glucoside |
| Rhizoma Bistortae | *Polygonum bistorta* L. | Polygonaceae | Bistort Rhizome | n/a |
| Rhizoma Menispermi | *Menispermum dauricum* DC. | Menispermaceae | Asiatic Moonseed Rhizome | n/a |
| Radix Scutellariae Baicalensis | *Scutellaria baicalensis* Georgi | Labiatae | Baical Skullcap Root | baicalein, baicalin, wogonin, wogonoside, neobaicalein, oroxylin aglucuronide, camphesterol, β-sitosterol, benzoic acid |
| | Vesica Fellea Bovus | | Bovine Biliary powder | n/a |
| Radix Astragali | *Astragalus membranaceus* (Fisch.) Bge. var. *mongholicus*. (Bge.) Hsiao or *Astragalus membranaceus* (Fisch.) Bge. | Leguminosae | Milkvetch Root | D-β-asparagine, 2',4'-dihydroxy-5,6-dimethoxyisoflavane, calycosin, formononetin, cycloastragenol, astragalosides, choline, betaine, kumatakenin, sucrose, glucoronic acid, β-sitosterol |
| Fructus Lycii | *Lycium barbarum* L. | Solanaceae | Barbary Wolfberry Fruit | betaine, carotene, physalien, thiamine, riboflavin, vitamin C, β-sitosterol, linoleic acid |
| Radix Notoginseng | *Panax noto-ginseng* (Burk.) F.H. chen, *P. pseudoginseng* Wall, *P. sanchi* Hoo. | Araliaceae | San-chi, notoginseng, Tian qi, Shen san qi | Arasaponin A, arasaponin B, dencichine |
| Radix Scrophulariae Ningpoensis | *Scrophularia ningpoensis* Hemsl. or *S.* | Scrophulariaceae | Figwort Root, Scrophularia | 1-asparagine, oleic acid, linoleic acid, |

TABLE 1-continued

Herbs of the Present Pharmaceutical Composition

| Pharmaceutical Name | Botanical/ Zoological Name | Family | Common Description | Major Ingredients |
|---|---|---|---|---|
| Fructus Schisandrae Chinensis | buergeriana Miq. Schisandra chinensis (Turcz.) Baill., S. sphenanthera Rehd. et Wils. | Magnoliaceae | Chinese Magnoliavine Fruit, schisandra fruit | stearic acid, carotene sesquicarene, β-bisabolene, β-chamigrene, α-ylangene, schizandrin, pseudo-γ-schizandrin, deoxyschizandrin, schizandrol, citral, stigmasterol, vitamin C, vitamin E |
| Tuber Curcumae | Curcuma wenyujin Y. H. Lee et C. Ling., or Curcuma Longa L., or Curcuma aromatica Salisb., or Curcuma zedoaria Rosc., or Curcuma kwangsiensis S. G. Lee et C. F. Liang | Zingiberaceae | Turmeric Root-tuber, curcuma | d-camphene, d-camphor, 1-α-curcumene, 1-β-curcumene, curcumin, demethoxycurcumin, bisdemethoxy-curcumin, turmerone, ar-turmerone, carvone, ρ-tolylmethyl-carbinoldiferuloyl-methane |
| Fructus Crataegi | Crataegus pinnatifida Bge.; C. pinnatifida Bge. var. major N.E. Br. or C. suneata Sieb. et Zucc. | Rosaceae | Hawthorn Fruit | crategolic acid, citric acid, tartaric acid, flavone, sugars, glycosides, vitamin C |
| Radix Angelicae Sinensis | Angelica sinensis (Oliv.) Diels | Umbelliferae | Chinese Angelica root, tang-kuei | butylidene phthalide, ligustilide, n-butylidene-phthalide, sequiterpenes, carvacrol, dihydrophthalic anhydride, sucrose, vitamin $B_{12}$, carotene, β-sitosterol |

Diffuse hedyotis or spreading hedyotis (Herba *Hedyotidis Diffusae*) belongs to the family of Rubiaceae. The entire plant is used as an herbal medicinal component. The herb has no toxicity. The herb is harvested in summer and autumn in mainland China and in late spring or early winter in Taiwan. In "Materia Medica" (Chinese Herbal medicine), compiled and translated by Dan Bensky & Andrew Gamble, diffuse hedyotidis clears heat and resolves dampness by promoting urination. It is particularly useful for relieving hot painful urinary dysfunction and damp-heat jaundice. Diffuse hedyotidis is the major ingredient in the present herbal pharmaceutical composition which contributes to the medicinal effect on liver diseases and HIV.

Bistort rhizome (Rhizoma Bistortae) is the dried rhizome of the plant *Polygonum bistorta* L. It belongs to the family of Polygonaceae. Bistort rhizome has moderate cool property (meaning that bistor rhizome is an "yang" herb). It can be used to remove toxic heat, to promote the subsidence of swelling and to stop bleeding.

Giant knotweed rhizome (Radix et Rhizoma *Polygoni Cuspidati*) is the dried rhizome and root of *polygonum cuspidatum* Sieb. et Zucc. It belongs to the family of Polygonaceae. The plant is grown throughout China, especially Jiangsu, Zhejiang, Anhui, Guangdong, Guangxi, Sichuan, and Guizhou provinces. The plant is harvested in spring and autumn. Giant knotweed rhizome is normally used to dispel damp, to eliminate blood stasis and alleviate pain, to relieve cough, and to resolve phlegm.

Chinese magnoliavine fruit (Fructus Schisandrae) is the dried ripe fruit of *Schisandra chinensis* (Turcz.) Baill. or *Schisandra sphenanthera* Rehd. et Wils. It belongs to the family of Magnoliaceae. The former, the best of its kind, is produced in northern parts of China and is habitually called "Northern schisandra fruit"; the latter is commonly referred to as the "Southern schisandra fruit" as it is produced in the southern parts of China. Both kinds can be used for the pharmaceutical preparation of the present invention. The fruit is collected in autumn and dried under the sun after removing the fruit stalks. Chinese magnoliavine fruit is generally used to arrest disharges, replenish qi, promote fluid secretion, tonify the kidney, and induce sedation. Chinese magnoliavine fruit can also decrease the level of GPT (glutamate-pyruvate transaminase) in patients with hepatitis.

Asiatic moonseed rhizome (Rhizoma Menispermi) is the dried rhizome of *Menispermum dauricum* DC. It belongs to the family of Menispermaceae. Asiatic moonseed rhizome has cool property. It can be used to remove toxic heat and relieve rheumatic pains.

Baical skullcap root (Radix Scutellariae) is the dried root of *Scutellaria baicalensis georgi*. It belongs to the family of Labiatae. The plant is produced in the provinces of Hebei, Shanxi, Inner Mongolia, etc., and collected in spring or autumn. Baical skullcap root is used to remove damp-heat, counteract toxicity, arrest bleeding, and prevent abortion, in patients.

Bovine biliary powder is the gallbladder of the cow, Vesica *Fellea Bovus*. It can clear heat and alleviate spasms.

Turmeric root-tuber (Radix Curcumae) is the dried root tuber of *Curcuma wenyujin* Y. H. Lee et C. Ling., or *Curcuma Longa* L., or *Curcuma aromatica* Salisb., or *Curcuma zedoaria* Rosc., or *Curcuma kwangsiensis* S. G. Lee et C. F. Liang. The herb is mainly produced in Sichuan, Zhejiang, Guangdong, and Guangxi provinces in China, and harvested in winter or spring, washed clean after the removal of the hairy rootlets, boiled thoroughly, and dried in the sun. It belongs to the family of Zingiberaceae. Turmeric root-tuber tastes bitter and had cool property. It can be used to clear heat, alleviate spasms and chest pain, and resolve phlegm.

Hawthorn fruit (Fructus Crataegi) is the dried ripe fruit of *Crataegus pinnatifida* Bge. var major N. E. Br., or *Crataegus pinnatifida* Bge., or *Crataegus cuneata* Sieb. It is produced primarily in Henan, Jiangsu, and Shandong provinces of China. It is harvested in autumn, sliced, and dried in sunlight. It belongs to the family of Rosaceae. Hawthorn fruit is normally used to stimulate digestion and promote the functional activity of the stomach. It can also improve the normal blood flow and dissipate blood stasis.

Sanqi, or San-chi, (Radix Notoginseng) belong to the family of *Araliaceae*. *Sanchi* (Sanqi) is the dried root of *Panax notoginseng* (Burk.) F. H. Chen. The plant is also known as *P. pseudoginseng* Wall and *P. sanchi* Hoo. The plant grows in Yunnan, Guangxi, Sichuan, Guizhou, and Jiangxi provinces of China, and is harvested in the autumn or winter of the third or seventh year, either before the flowers bloom (better) or after the fruit is ripe. H. Gao et al., *Pharmaceutical Research*, (1996) 13(8): 1196–1200, disclose that polysaccharides from *Panax notoginseng* (San-Chi) have immuno-stimulating activities in vitro.

Barbary wolfberry fruit (Fructus Lycii) is the dried ripe fruit of *Lycium barbarum* L. It belongs to the family of Solanaceae. The plant is mainly produced in Ningxia, Gansu, and Qinghai provinces of China. It is harvested in summer and autumn. It nourishes and tonifies the liver and kidneys. It can also replenish vital essence and improve eyesight.

Figwort Root (Radix Scrophulariae) is the dried root of *Scrophularia ningpoensis* Hemsl. It belongs to the family of Scrophulariaceae. The herb is chiefly produced in Zhejiang and Sichuan provinces of China and harvested in winter when the part of the plant above-ground has withered. The roots are piled and dried in sunlight alternately until the inside becomes black and then sliced for use. Figwort root can reduce heat from blood. It als has nourishing capacity and can counteract toxicity.

Chinese angelica (Radix *Angelicae Sinensis*) is the dried root of *Angelica sinensis* (Oliv.) Diels. It belongs to the family of Umbelliferae. The herb is mainly produced in Gansu and Shanxi provinces of China. It is harvested in late autumn, smoked dry on slow fire after getting rid of the rootlets, sliced, or stir-baked with wine. Chinese angelica can enrich blood, promote blood circulation, regulate menstruation, relieve pain, and relax bowels.

Milkvetch root (Radix Astragali) is the dried root of *Astragalus membranaceus* (Fisch.) Bge. var. *mongholicus*. (Bge.) Hsiao or *Astragalus membranaceus* (Fisch.) Bge. It belongs to the family of Leguminosae. The herb is mainly produced in Shanxi, Gansu, Heilongjiang, and Inner Mongolia of China. The plant of four-year old or older is harvested in spring or autumn. Milkvetch root can promote discharge of pus and the growth of new tissue.

The pharmaceutical composition of the present invention is suitable for preparation in a scale typical for pharmaceutical industry as well as for smaller measure.

In the process for making the pharmaceutical composition of the present invention, the individual herbal components are pretreated according to the common procedures. The herbs are cut and put in a container with water to boil and simmer twice. The first time of simmering takes two hours, the solution is collected, and water is added for the second time of simmering for about 1.5 hour. The solutions from the simmering steps are collected and then filtered by a sieve/filter. The filtrate is then condensed from about 1.4 fold by volume to about 1.0 fold by volume. The resulting condensate is pasty-like. Optionally, the herbs can be simmered, filtered and condensed again. The second condensate is then mixed with the first condensate to form the "HIVCIDE condensate," which becomes the basic content of the HIVCIDE injection solution. When used, the HIVCIDE injection solution is further diluted 1:5 to 1:10 by volume with a suitable solution. The gram weight of the HIVCIDE injection solution described herein is referred to the weight of the "HIVCIDE condensate."

The following example is illustrative, but not limiting the scope of the present invention. Reasonable variations, such as those occur to reasonable artisan, can be made herein without departing from the scope of the present invention.

EXAMPLE 1

Pharmaceutical Preparation of HIVCIDE

The kinds and amounts of the herbal ingredients used in the process of making the pharmaceutical composition of the present invention are described in Table 1. The pharmaceutical composition is called "HIVCIDE," which is named after "HIV-killer" ("-cide" means "killer"). HIVCIDE was formulated as injection solution and capsules.

Table 2. Ingredients Used in Making HIVCIDE Injection Solution and Capsules

| Component | Amount (kg) |
|---|---|
| Diffuse hedyotis | 3.32 |
| Bistort Rhizome | 2.49 |
| Giant Knotweed root and Rhizome | 0.83 |
| Asiatic Moonseed Rhizome | 0.83 |

-continued

| Component | Amount (kg) |
|---|---|
| Baical Skullcap Root | 0.83 |
| Bovine Biliary powder | 0.083 |
| Milkvetch Root | 1.66 |
| Barbary Wolfberry Fruit | 2.49 |
| Sanchi | 0.83 |
| Figwort root | 1.66 |
| Chinese Magnoliavine Fruit | 1.66 |
| Turmeric Root-tuber | 0.83 |
| Hawthorn fruit | 1.66 |
| Chinese Angelica | 0.83 |

(1) Quality Controls of Raw Materials

Quality control tests carried out for each individual raw material were according to conventional methods used in the herbal pharmaceutical field, which include, but are not limited to, physical appearance, loss on drying, total ash, acid insoluble ash, alcohol extracts, water extracts, TLC, HPLC, heavy metals, microbial counts and residual pesticides. Bovine biliary powder was tested for appearance, TLC and general chemistry.

(2) Manufacturing Process

The individual herbal components were pretreated according to common procedures. The herbs were weighed according to Table 2. A flowchart of the manufacturing process for making HIVCIDE injection solution is provided in Table 3:

TABLE 3

Manufacturing Process For Making HIVCIDE

| Manufacturing Process | Quality Control Procedure |
|---|---|
| Raw Herbs Delivered | Quality Control of Raw Herbs: |
|  | Physical Appearance |
| ↓ |  |
| Preparation (cutting, drying, etc.) |  |
| ↓ | Quality Control of Raw Herbs: |
|  | Physical Appearance |
|  | Loss on Drying |
| Obtain Total of 20.003 kg Raw Herbs and Put into Extractor for Manufacturing | Total Ash |
|  | Acid Insoluble Ash |
|  | Alcohol Extracts |
|  | Water Extracts |
|  | TLC |
|  | HPLC |
|  | Heavy Metals |
| Add 350 L ± 10% Water to Soak Herbs in Extractor for 60 ± 10 min | Microbial |
|  | Residues Pesticide |
|  | Note: Bovine biliary powder (also known as Bovis Bezoar) is only tested for appearance, TLC and General Chemistry |
| ↓ |  |
| 1st Extraction Parameter Set: |  |
| 1. Dial Set Temperature at 95° C. with the Acceptable Range of 90° C.–100° C. | In-Process Quality Control: (take 10–15 g as test sample) Concentration of Solid Content Concentration of Water |
| 2. Dial Set Steam Pressure at 2 kg/cm². |  |

TABLE 3-continued

Manufacturing Process For Making HIVCIDE

| Manufacturing Process | Quality Control Procedure |
|---|---|
| 3. Dial Read Out the Lid Pressure at 0.2–0.4 kgf/cm² Range. | Content |
| 4. Extract for 45 minutes. |  |
| ↓ Liquid Extract |  |
| 1st Concentration Parameter Set: |  |
| 1. Dial Read Out Vacuum at −60~76 cmHg. |  |
| 2. Dial Read Out Temperature at 40° C. ± 5° C. |  |
| 3. Process for 40 minutes. |  |
| ↓ |  |
| Raw Herbs Add Water 350 L ± 10% |  |
| 2nd Extraction Parameter Set: |  |
| 1. Dial Set Temperature at 95° C. with the Acceptable Range of 90° C.–100° C. |  |
| 2. Dial Set Steam Pressure at 2 kg/cm². |  |
| 3. Dial Read Out the Lid Pressure at 0.2–0.4 kgf/cm² Range. |  |
| 4. Extract for 45 minutes |  |
| ↓ Liquid Extract |  |
| 2nd Concentration Parameter Set: |  |
| 1. Dial Read Out Vacuum at −60–76 cmHg. |  |
| 2. Dial Read Out Temperature at 40° C. ± 5° C. |  |
| 3. Process for 40 minutes. |  |
| ↓ |  |
| Combined Concentrated Extracts and Pour into the Stainless Container Final Yield: 6.1 kg ± 10% Spraying Silo Parameter Set: |  |
| 1. Dial Set Temperature at 60° C. |  |
| 2. Pre-heat for 15 minutes. |  |
| ↓ |  |
| Fluid Bed Dryer |  |
| 1. Add 3.9 kg of Starch (adj. Base on water content of the starch). |  |
| 2. Dial Set In-Temperature at 60° C.; Out-Temperature at 50° C. |  |
| 3. Pre-heat for 10 minutes. |  |

TABLE 3-continued

Manufacturing Process For Making HIVCIDE

| Manufacturing Process | Quality Control Procedure |
|---|---|
| 4. Process for target of 2 hours ± 20 min. until LOD <5%. | |
| Yield 9.5 kg~ 10.5 kg ↓ | |
| Sievinig Parameter Set: | |
| 1. Dial Read out Temperature at 23 ± 4° C.<br>2. Dial Read out RH at 50 ± 10%.<br>3. Sieve with #100 followed by #80. | |
| Yield 9.0 kg~ 10.5 kg ↓ | |
| HIVCIDE Powder | Quality Control of Drug Substance:<br>Physical Appearance<br>Loss on Drying<br>Total Ash<br>Acid Insoluble Ash<br>Alcohol Extracts<br>Water Extracts<br>TLC<br>HPLC<br>Heavy Metals<br>Microbial<br>Residues Pesticide<br>Stability |

The individual herb was cut into small pieces and thoroughly mixed together. The mixed herbs were placed in bags with sufficient space to spread out. The bags were placed in an extractor with 350 L (±10%) of water and soaked for about 60±10 min. The herbs were first extracted at 95±5° C. under steam pressure of 2 kg/cm$^2$ and lid pressure of 0.2–0.4 kg/cm$^2$ for 45 min. The water extract was collected into a concentrator and concentrated at 40±5° C. under vacuum of −60 to −76 cmHg for 40 min to form the first concentrate.

The herbs in the bags were recovered from the extractor, placed into another 350 L (±10%) of water and extracted again at 95±5° C. under steam pressure of 2 kg/cm$^2$ and lid pressure of 0.2–0.4 kgf/cm$^2$ for 45 min. The extract from the second extraction was collected into a concentrator and concentrated at 40±5° C. under vacuum of −60 to −76 cmHg for 40 min to form the second concentrate.

The first and second concentrates were combined and poured into a stainless container. The total weight of the combined concentrates was about 6.1 kg±10%. The combined 1$^{st}$ and 2$^{nd}$ concentrates were called the "HIVCIDE condensate."

For the HIVCIDE injection solution, about 0.1 to 1 g, preferably 0.4 g of the "HIVCIDE condensate" was dissolved in about 1 ml of the injection buffer. About 5 ml of the injection solution was poured into an ampoule.

For the HIVCIDE powders (which were packaged into HIVCIDE capsule), about 3.9 kg of starch (adjustable based on the water content of the starch) were added to the HIVCIDE condensate and spray dried in a fluidized bed setting at in-temperature of 60° C. and out-temperature of 50° C. for approximately 120±20 min until LOD (limit of detection)<5%.

The resultant powders were passed through a 100-mesh sieve and then a 80-mesh sieve. The final yield of the HIVCIDE powders were about 9.5~10.5 kg. The HIVCIDE powders were further packaged into capsules. Any conventional capsules, including, but not limited to, natural gelatin, pectin, casein, collagen, protein, modified starch, and polyvinyl pyrrolidone, were suitable for encapsulation.

There were two dosage forms of HIVCIDE capsules: A 500 mg of the HIVCIDE capsule, which contained about 305 mg of the "HIVCIDE condensate" and about 195 mg of starch; and a 220 mg of the HIVCIDE capsule, which contained about 134 mg of the "HIVCIDE condensate" and about 86 mg of starch.

(3) In-Process Quality Controls

After the extracts were concentrated, a 10–15 g sample was collected and the concentrations of the solid content and the water content were determined by methods described in US Pharmacopoeia, China Pharmacopoeia, and/or Japanese Pharmacopoeia.

EXAMPLE 2

Acute Toxicity Study of HIVCIDE in Animals

Purpose:

The following experiment was conducted at the Toxicology Laboratory of the Institute of Labor, Health, and Occupational Disease of Heilungkiang Province in China to examine acute toxicity of the HIVCIDE during intravenous injection in animals.

Methods:

Experimental animals were Japanese big-ear white rabbits obtained from the Animal Center of Haerbin Medical University in Haerbin, Heilungkiang Province, China. These rabbits were characterized by the obvious blood vessels on ears which facilitates the operation of injection during the experiments.

Ten (10) rabbits were obtained including six (6) males and four (4) females, each weighing between 1900 g to 3000 g.

The rabbits were randomly divided into two (2) groups, five rabbits in each group including two (2) females and three (3) males. The HIVCIDE injection solution was intravenously injected into the two groups of rabbits through the veins on their ears at dosages of 10 g and 15 g of HIVCIDE condensate per kg of rabbit body weight, respectively.

The HIVCIDE concentration was about 1 g/ml, so that the higher dosage group was about 15 ml/kg, which was roughly equal to a sixty (60) kg-weighted adult treated with 900 ml of the HIVCIDE injection solution.

The rabbits were observed for behaviour continuously for a period of two (2) weeks after intravenous injections. Observation was conducted hourly at day 1; during the following days, observation was conducted four to six (4–6) times per day.

At the end of the observation period, rabbits were sacrificed and dissected to examine the eyes, liver, lung, and spleen to determine adverse effects.

Results:

No abnormal behavior was found in the rabbits during the entire observation period. All animals exhibited normal body weight gains. No organ abnormality was observed. After sacrifice and dissection of the animals, inspection of the eyes, liver, lung, and spleen showed no extraordinary syndromes. The results indicate that, when comparing with the general acute toxicity index, the HIVCIDE injection solution showed no symptoms of acute or chronic toxicity.

Conclusion:

The intravenous administration of HIVCIDE injection solution up to 15 g/kg was well-tolerated, which was approximately equal to injection of 900 ml of HIVCIDE into a 60-kg of human. The HIVCIDE demonstrated no acute toxicity in rabbits.

EXAMPLE 3

Effects of the HIVCIDE on HIV in Cell Cultures

Purpose:

The following experiment was to determine the effectiveness of the HIVCIDE injection solution gainst HIV in cell cultures.

Methods:

MT4 cells were cultured in HIV-1 suspension liquid of 100 $TCID_{50}$ in a 96-orifice culture plate. MT4 is a human T-cell lymphotropic virus type 1-transformed cell line. The culture condition was set at a temperature of 37° C. and under 5% $CO_2$. The duration of the culture was seven (7) days.

The HIVCIDE injection solution of the present invention was added to the cultural wells at various concentrations. The morphology of the MT4 cells was observed under microscope by conventional methods.

Results:

No pathological changes of MT4 cells were observed in the cultural wells where the HIVCIDE injection solution was added to in adequate concentrations. The inhibition of the pathological changes of MT4 cells indicated that the HIVCIDE injection solution had inhibitory effect on pathological changes of the cultured cells caused by HIV.

The effective concentration of the HIVCIDE injection solution for inhibition of the pathological changes of MT4 cells was more than 12.5 mg/ml. To achieve a 50% of inhibition, the concentration of the HIVCIDE herbal composition was 25 mg/ml.

Conclusion:

The HIVCIDE injection solution was effective in inhibiting pathological changes in cells caused by HIV-1 in vitro.

EXAMPLE 4

A Case Study on an HIV-Patient Treated with HIVCIDE

Purpose:

The following clinical trial was conducted in the Infectious Disease Hospital in Shanghai, China to test the effectiveness of the herbal composition of the present invention in treating an HIV-infected patient.

Methods:

A fifty-year Chinese male patient diagnosed with HIV infection complicated by herpes zoster was treated with anti-virus regimens by the combination of western medicine and the herbal composition of the present invention during hospital stay.

Results:

The patient was confirmed of HIV-infection by Rapid Agglutinin Assay. At the time of the initial diagnosis, the patient showed no symptoms. Ten months after the initial diagnosis, the patient quickly developed an herpetiform rash over the front of the left side of the check extending over the nick, the shoulder, and the upper left arm. The patient was then admitted into the Hospital shortly thereafter.

At the hospital, the result of the physical examination was normal except the skin rash. The pathology tests confirmed normal renal function. The functional tests of the liver showed a slightly increased level of serum γ glutamyl transpeptidase and acetyl glucuronidase. Hepatitis viral tests showed negative for Hepatitis B virus and Hepatitis C virus (HBV-DNA and HCV-RNA). However, Hepatitis G viral test showed positive for HGV-RNA. The immunological studies showed that the β-2 microglobulin level was 2.4–2.5 mg/ml.

During the hospital stay, haemoglobin and erythrocytes levels of the patient were slightly decreased, while the levels of the leukocyte and platelet were normal. Peripheral blood lymphocytes counts showed that T4 cells were decreased to 2.76×10/L (32.9%) and the ratio of T4/T8 cell was 1.16. Thus, the diagnosis is that the patient was with HIV infection complicated by herpes zoster.

During hospital stay, the patient had diarrhea and dry cough for a few days and was cured. The patient showed HIV antibody positive by ELISA, and his T4 cells further decreased to 25.4% and the ratio of T4/T8 cells was inverted to 0.94.

The patient's T4 cells and the ratio of T4/T8 gradually increased after intravenously injected with the HIVCIDE injection solution. In about three months of HIVCIDE treatment, his T4 cells were returned to 40.7%, and the ratio of T4/T8 was improved to 1.45. The skin rash gradually disappeared and completely recovered by the end of November.

Conclusion:

The HIVCIDE injection solution was effective in reducing symptoms of the HIV-infected patient in a treatment regime together with western medicine.

EXAMPLE 5

Clinical Study of Five HIV-Positive Patients Treated with HIVCIDE Injection Solution Purpose:

The following clinical trial was conducted in De-Tang Hospital (National AIDS Therapy Center) in Beijing, China to test the effectiveness of HIVCIDE in HIV patients.

Methods:

Five (5) HIV-postive patients were intravenously injected with HIVCIDE daily. The HIV infection was confirmed by western blotting. The profile of the patients are shown in Table 4:

TABLE 4

Medical Profile of the HIV Patients Participated in the Clinical Study

| Patients | Gender | Age | History | Diagnosis |
|---|---|---|---|---|
| 1 | Male | 32 | 2 years | AIDS (Stage IV) |
| 2 | Male | 25 | 0.5 year | AIDS (Stage II) |
| 3 | Female | 32 | 1 year | AIDS (Stage IV) |
| 4 | Male | 31 | 1 year | AIDS (Stage III) |
| 5 | Male | 17 | 3 weeks | HIV acute infection |

The patients were treated according to the following regimen:

The HIVCIDE injection solution was prepared according to EXAMPLE 1, supra. Prior to the injection, five (5) ml of HIVCIDE injection solution was diluted in 250 ml of 5% glucose solution. The diluted solution was injected intravenously once per day for three (3) consecutive days. If no adverse reactions were observed, the dosage was increased to 15 ml of HIVCIDE in 250 ml of 5% glucose solution, and the patients were injected intravenously once per day reactions for two (2)-three (3) months.

Additionally, patient #1 was treated with AZT and DDI therapy for 3 months. The AZT and DDI therapy was discontinued ten (10) days prior to the HIVCIDE treatment. Patients #2, #3, and #4 were given HIVCIDE daily injection alone. Patient # 5 was given combined treatment of α-interferon and HIVCIDE.

About 3 ml of blood sample were taken from the patients each time before, during, and after the treatment and further tested for HIV numbers. CD4 counts were determined in Patients #1, #2 and #4 before and after the respective treatment.

Results:

No adverse reactions to the HIVCIDE injection solution were observed. Three out of the four AIDS patients had different degrees of fatigue before the treatment of HIVCIDE. There was marked improvement in the fatigue after the treatment with HIVCIDE in the three AIDS patients.

Figure 1:
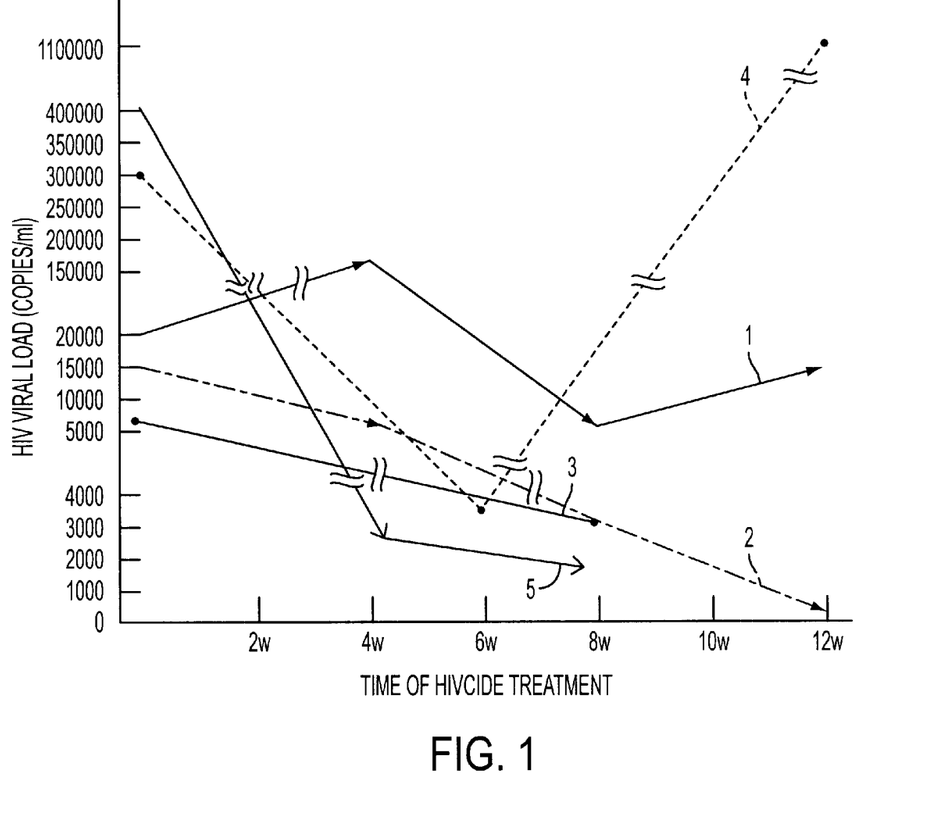

The change in HIV viral load (copies/ml) in plasma before and after HIVCIDE treatment is shown in Table 5 and FIG. 1.

TABLE 5

Change In HIV Viral Load In Plasma of HIV-Positive Patients

| Patients | before treatment | 1st month during treatment | 2nd month during treatment | 3rd month, at the end of treatment |
|---|---|---|---|---|
| 1 | $1.9 \times 10^{4*}$ | $1.7 \times 10^5$ | $6.3 \times 10^3$ | $1.5 \times 10^4$ |
| 2 | $1.5 \times 10^4$ | $6.3 \times 10^3$ | | $3.8 \times 10^2$ |
| 3 | $7.3 \times 10^3$ | | $3.2 \times 10^3$ | |
| 4 | $3.0 \times 10^5$ | | $3.7 \times 10^{3***}$ | $1.1 \times 10^6$ |
| 5** | $3.9 \times 10^5$ | $2.6 \times 10^3$ | $1.8 \times 10^3$ | |

*The lower HIV numbers observed in Patient #1 before treatment might be contributed to the 3-month treatment of AZT and DDI prior to the start of HIVCIDE treatment.
**Patient #5 received concurrent treatment of HIVCIDE and α-interferon.
***The plasma HIV viral load of Patient #4 was detected 6 weeks after the HIVCIDE treatment.

As shown in Table 5 and FIG. 1, four of the five HIV-positive patients (i.e., patients #1, #3, #4, and #5) showed decrease in HIV viral load in two months. Two out of these four patients (i.e., patients #1 and #4) showed a rebound in viral load after the end of the third-month HIVCIDE treatment. The other two patients, (i.e., patients #3 and #5), showed significant clinical symptom relief, and did not provide plasma sample for analysis at the end of the third-month treatment. Patient #2, whose plasma sample was not taken at the end of the second month treatment, showed a 40-time reduction in HIV viral load at the end of the third-month HIVCIDE treatment. Patient #2 also demonstrated significant clinical symptom relief at the end of the third-month HIVCIDE treatment. However, because patient #5 received concurrent treatment with α-interferon, the results of this patient were difficult to assess.

The results of the HIV viral load study indicate that all of the patients demonstrated reduction in HIV viral load after HIVCIDE treatment. However, great fluctuation in the replication of HIV was observed in two of the five patients. For example, patient #4's HIV viral load decreased significantly after 6 weeks of treatment but rebounded after the end of the three-month HIVCIDE treatment. Patient #1 also experienced a rebound (although to a much lesser degree than that of patient #4) at the end of the third-month treatment.

In addition to HIV viral load, CD4 count (count/mm$^3$) was measured in three patients (i.e., patients #1, #2, and #3) at the end of the three-month HIVCIDE treatment. For example, the CD4 count of patient #2 rose from 285 to 510/mm$^3$ after 3 months of HIVCIDE treatment and continued to rise to 630/mm$^3$ 2 months after the discontinuance of the HIVCIDE treatment. The CD4 count of Patient 4 was 190/mm$^3$ prior to HIVCIDE treatment, 40/mm$^3$ after 3-month of HIVCIDE treatment, and 360/mm$^3$ 2 months after the discontinuance of the HIVCIDE treatment.

Conclusion:

The results indicated that HIVCIDE injection solution was effective in treating HIV/AIDS patients.

EXAMPLE 6

Clinical Study of HIV-Positive Patients with HIVCIDE and HIVCIDE Capsules Treatment in Russia Purpose:

The following experiment was conducted in Hospital in Siberia, Russia to examine the effectiveness of the HIVCIDE injection solution and HIVCIDE capsules against HIV infection.

Methods:

Five (5) HIV-Positive patients were treated with the HIVCIDE injection solution and HIVCIDE capsules obtained from Gongming Pharmaceutical Co., Ltd, Heilongkiang Province, China. The HIVCIDE injection solution and HIVCIDE capsules were prepared according to EXAMPLE 1, supra.

The profile of the patients are shown in Table 6:

TABLE 6

Medical Profile of the HIV-Positive Patients Participated in the Clinical Study in Russia

| Patients | Gender | Age | History | Diagnosis |
|---|---|---|---|---|
| 1 | Female | 23 | 2 years | AIDS (Grade A3), adenitis, hepatitis C, Syphilis, Citomegalo infection, Gonorrhea |
| 2 | Female | 28 | 2 year | AIDS (Grade A3), adenitis, hepatitis B and C, Gerdeo and Citomegalo infection, Gonorrhea, drug abuse |
| 3 | Male | 35 | 1 year | AIDS (Grade B2), adenitis |
| 4 | Male | 22 | 1 year | AIDS (Grade B2), adenitis, hepatitis C, drug abuse |
| 5 | Male | 34 | several months | AIDS (Grade A3), adenitis, hepatitis B and C, 10% weight loss, drug abuse |

The patients were concurrently treated with HIVCIDE injection solution and HIVCIDE capsules. For HIVCIDE injection solution, about 5 ml of HIVCIDE injection solution (containing approximately 0.4 g of HIVCIDE condensate per ml) were diluted in 250 ml of 5% glucose. Each patient was given an intravenous injection of the HIVCIDE injection solution once daily for 3 months. For HIVCIDE capsules, each patient was given 6 HIVCIDE capsules (220 mg of HIVCIDE capsules) per time (before meal), three times per day for 3 months.

Blood samples were taken from the patients before, during, and after the HIVCIDE treatment for tests of CD4 cells count.

Results:

All patients experienced pain in the stomach and right rib area during the first two weeks of the treatment period.

Patient #5 also vomited every morning for a week in the third month of the treatment period.

The CD4 cells count of the patients is shown in Table 7:

TABLE 7

Change in CD4 Cells Count in Patients With HIV Infection

| Patients | before treatment | 2nd month during treatment | 2 months after the completion of the 3-month treatment |
|---|---|---|---|
| 1 | 477 | 641 | 849 |
| 2 | 740 | 1140 | 705 |
| 3 | 421 | — | 527 |
| 4 | 440 | 490 | 669 |
| 5 | 625 | — | 814 |

During the treatment period, all patients demonstrated positive response to the HIVCIDE treatment except the minor adverse reactions as mentioned above. The physical condition of all of the patients had clearly improved after one month of the HIVCIDE treatment. In particular, patients felt stronger, were happier and showed improved appetite. Anaphylaxis, melancholy, stomach pain and discomfort disappeared. For some of the patients who had constipation, the symptom was greatly improved. For some of the patients who had experienced insomnia, the sleepless problem was also greatly improved. Also, patients #4 and #5 had gained about 5 kg at the end of the three-month HIVCIDE treatment. And patients # 2 and #4 stopped taking narcotic analgesics for pain relief. The biochemical indicators, including HBV and HCV, in some of the patients were also clearly improved. The M antibody in Citomegalo virus, genorrhea antibody and HBC antibody also disappeared.

Also, as shown in the last column of Table 7, 2 months after the completion of the 3-month treatment period, all of the patients CD4 cell counts were continued to increase, which indicated that no relapse had occurred after the termination of the HIVCIDE.

Patients #1 and #2 had received a second 3-month course of HIVCIDE treatment after the completion of the first 3-month HIVCIDE program. No adverse effect was observed at the end of the second course of HIVCIDE treatment.

Conclusion:

The combined use of HIVCIDE injection solution and HIVCIDE capsules was effective in reducing symptoms in HIV-positive patients.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A pharmaceutical composition for treating patients with human immunodeficiency virus (HIV) infection comprising effective amounts of a mixture of aqueous extracts obtained from:

an entire plant of Herba *Hedyotidis diffusae* (diffuse hedyotis);

a rhizome of Rhizoma Bistortae (bistort rhizome);

a rhizome of Rhizoma *Polygoni Cuspidati* (giant knotweed rhizome);

a ripe fruit of Fructus Schisandrae (Chinese magnoliavine fruit);

a rhizome of Rhizoma Menispermi (Asiatic moonseed rhizome);

a root of Radix Scutellariae (baical skullcap root); bovine biliary powder;

a root tuber of Radix Curcumae (tumeric root-tuber);

a ripe fruit of Fructus Crataegi (hawthorn fruit);

a root of Radix Notoginseng (sanqi);

a ripe fruit of Fructus Lycii (barbary wolfberry fruit);

a root of Radix Scorphulariae (figwort root);

a root of Radix *Angelicae sinensis* (Chinese angelica); and a root of Radix Astragali (milkvetch root), wherein said pharmaceutical composition does not contain Radix *ginseng rubra* (red ginseng).

2. The pharmaceutical composition according to claim 1, wherein said aqueous extract of said ingredients is a water extract of said ingredients.

3. The pharmaceutical composition according to claim 2, wherein said water extract is further filtered and condensed to form a condensate.

4. The pharmaceutical composition according to claim 1, wherein said diffuse hedyotis, said bistort rhizome; said giant knotweed rhizome, said Chinese magnoliavine fruit, said Asiatic moonseed rhizome, said baical skullcap root, said bovine biliary powder, said tumeric root-tuber, said hawthorn fruit, said sanqi, said barbary wolfberry fruit, said figwort root, said Chinese angelica, and said milkvetch root are at a weight ratio of about 4:3:1:2:1:1:0.1: 1:2:1:3:2:1:2.

5. The pharmaceutical composition according to claim 1, wherein said pharmaceutical composition is in a form of an intravenous injection solution.

6. The pharmaceutical composition according to claim 1, wherein said pharmaceutical composition is in a form of powders.

7. The pharmaceutical composition according to claim 6, wherein said powders are encapsulated.

8. A method for preparing the pharmaceutical composition according to claim 1 comprising:

grinding and mixing said diffuse hedyotis, said bistort rhizome, said giant knotweed rhizome, said Chinese magnoliavine fruit, said Asiatic moonseed rhizome, said baical skullcap root, said bovine biliary powder, said tumeric root-tuber, said hawthorn fruit, said sanqi, said barbary wolfberry fruit, said figwort root, said Chinese angelica, and said milkvetch root to form a mixture;

boiling said mixture in water to form a water extract;

filtering said water extract to collect a filtrate; and concentrating said filtrate to form a condensate; wherein said condensate is dissolved in a solution to form an injection solution or sprayed dried to form powders.

9. The method according to claim 8, wherein said filtrate is about 1.4 fold of the volume of said condensate.

10. The method according to claim 8, wherein said intravenous injection solution is further diluted to about 1:5 to 1:10 by volume of a 5% glucose solution.

11. The method according to claim 8, wherein said powders are mixed with starch and encapsulated.

12. A method for treating patients with HIV comprising:

intravenously administering to said patients an effective amount of said condensate of said pharmaceutical composition according to claim 3.

13. The method according to claim 12, wherein said injection solution is in a dosage amount of about 1 to 10 g of said condensate per day.

14. The method according to claim 13, wherein said injection solution is in the dosage amount of about 2 to 6 g of said condensate per day.

15. A method for treating patients with HIV infection comprising:
intravenously administering an injection solution and orally administering a capsule to said patients;
wherein said injection solution and said capsule each comprise said condensate of said pharmaceutical composition according to claim 3.

16. The method according to claim 15, wherein said injection solution is in a dosage amount of about 1 to 10 g of said condensate per day.

17. The method according to claim 16, wherein said injection solution is in the dosage amount of about 2–6 g of said condensate per day.

18. The method according to claim 15, wherein said capsule is in a dosage amount of about 0.1 to 2 g of said condensate of said pharmaceutical composition per serving and at about 2–4 times a day.

* * * * *